United States Patent [19]
Kalnajs et al.

[11] Patent Number: 5,418,879
[45] Date of Patent: May 23, 1995

[54] DISTRIBUTED LIGHT DELIVERY SYSTEM

[75] Inventors: Andrejs K. Kalnajs, Madison, Ala.;
Rolf H. Mueller, Auburn, N.Y.

[73] Assignee: Chrysler Corporation, Highland Park, Mich.

[21] Appl. No.: 222,757

[22] Filed: Apr. 4, 1994

[51] Int. Cl.⁶ .............................................. G02B 6/04
[52] U.S. Cl. .................... 385/115; 385/116; 385/901; 362/32
[58] Field of Search ............ 385/115, 901, 116; 362/32, 298; 356/237; 382/8

[56] References Cited
U.S. PATENT DOCUMENTS

| | | | |
|---|---|---|---|
| 4,604,648 | 8/1986 | Kley | 358/101 |
| 4,677,473 | 6/1987 | Okamoto et al. | 358/101 |
| 4,677,531 | 6/1987 | Szeles | 362/32 |
| 4,695,157 | 9/1987 | Schoenbaum et al. | 356/237 |
| 4,845,596 | 7/1989 | Mouissie | 385/115 X |
| 4,849,645 | 7/1989 | Mendenko et al. | 250/363 |
| 4,897,771 | 1/1990 | Parker | 362/298 |
| 5,000,535 | 3/1991 | Churchill | 350/96 |
| 5,058,985 | 10/1991 | Davenport et al. | 385/115 |
| 5,060,065 | 10/1991 | Wasserman | 358/106 |
| 5,102,227 | 4/1992 | Zwirner et al. | 356/384 |
| 5,103,385 | 4/1992 | Federico et al. | 362/298 |
| 5,109,461 | 4/1992 | Churchill | 385/115 |
| 5,153,668 | 10/1992 | Katzir et al. | 356/237 |
| 5,185,638 | 2/1993 | Conzola et al. | 356/237 |
| 5,319,731 | 6/1994 | Eastman | 385/115 |

Primary Examiner—Rodney B. Bovernick
Assistant Examiner—Phan T. H. Palmer
Attorney, Agent, or Firm—Margaret A. Dobrowitsky

[57] ABSTRACT

A distributed light delivery system for the illumination of printed circuit boards during fault detection operations is provided. The system has at least one light delivery bar having at least two optical light lines. Each optical light line is composed of an array of optical fibers. The entire array of optical fibers are oriented within the light delivery bar at one of at least two predetermined angles. When the light bar is properly mounted and directed on a staging apparatus, the light delivery bar is effective to illuminate all four sides and the top of three-dimensional components. The distributed light delivery system thus provides uniform and substantially shadow-free illumination of discrete through-hole technology components inserted through printed circuit boards, solder paste screened onto bare circuit boards, and/or SMD technology components mounted on printed circuit boards.

9 Claims, 3 Drawing Sheets

DISTRIBUTED LIGHT DELIVERY SYSTEM

FIELD OF INVENTION

The present invention relates to a fiber optic light delivery system for illuminating objects during circuit board fault inspection operations. More particularly, the present invention relates to a novel apparatus and method for providing shadow-free illumination of discrete through-hole technology components inserted through printed circuit boards, solder paste screened onto bare circuit boards, and/or surface-mounted device (SMD) technology components mounted on printed circuit boards.

BACKGROUND OF THE INVENTION

Machine vision inspection systems detect errors on printed circuit boards that occurred during the process of applying solder paste onto the bare boards. Machine vision inspection systems also detect geometry and placement errors that occurred during the process of automatically or manually populating the circuit boards with component parts. Such errors, theoretically perceptible by the human eye, include whether leads of discrete through-hole technology components have been correctly inserted through the proper solder paste pads on the circuit board. Other errors include the presence or absence of components, translational or rotational errors in the placement of the SMDs relative to the pad, and whether the SMDs were placed on their respective pads on the correct face. Machine vision inspection systems also measure the lead length and wipe angle of through-hole technology components and the various geometric characteristics of SMD technology components.

Machine vision inspection systems typically employ video cameras to capture visible spectrum images of the subject printed circuit boards. The video cameras are mounted on either a fixed or movable staging structure above an automated conveyor or a printed circuit board shuttle. The video cameras capture images of the printed circuit boards as they pass under the camera staging apparatus on the conveyor or shuttle. The captured images are first digitized, then compared to a master database of ideal art work to determine whether any of the above-mentioned geometry or placement errors are present.

Adequate and properly directed illumination of the screened solder paste and/or the through-hole and SMD components mounted on the subject circuit boards is critical to gathering accurate input data for the computer algorithm that correlates the digitized video camera image with the ideal art work. Adequate and properly directed illumination is also critical to the detection of all the errors present on each circuit board.

In the past, light has been delivered "straight-on" to the circuit board components within the video cameras' field of view from four discrete xenon lamps that were positioned parallel to the sides of the printed circuit board, as illustrated in FIG. 4 and described below. This straight-on approach proves disadvantageous because too much space is required to accommodate the four discrete light sources. More importantly, the straight-on approach fails to achieve shadow-free illumination of all four sides and the top of the essentially cubical SMD technology components. The straight-on approach fails to achieve shadow-free illumination because, except for the few components centered within the light sources, each xenon lamp is necessarily closer to some components and farther away from others disadvantageously resulting in shadows and bright spots across the printed circuit board.

SUMMARY OF THE INVENTION

It is therefore an object of the present invention to provide uniform and substantially shadow-free illumination of solder paste screened onto bare circuit boards, through-hole technology components inserted through circuit boards, and SMD technology components mounted on circuit boards.

In accordance with this object, a distributed light delivery system is provided having at least one housing bar with at least two optical light lines. Each optical light line is composed of an array of optical fibers oriented within the light bar at one of at least two predetermined angles. The optical fibers, thus oriented within the housing bar, are effective to illuminate all four sides and the top of three-dimensional SMD technology and discrete through-hole technology components.

DETAILED DESCRIPTION OF THE PREFERRED EMBODIMENT

Figure 1:
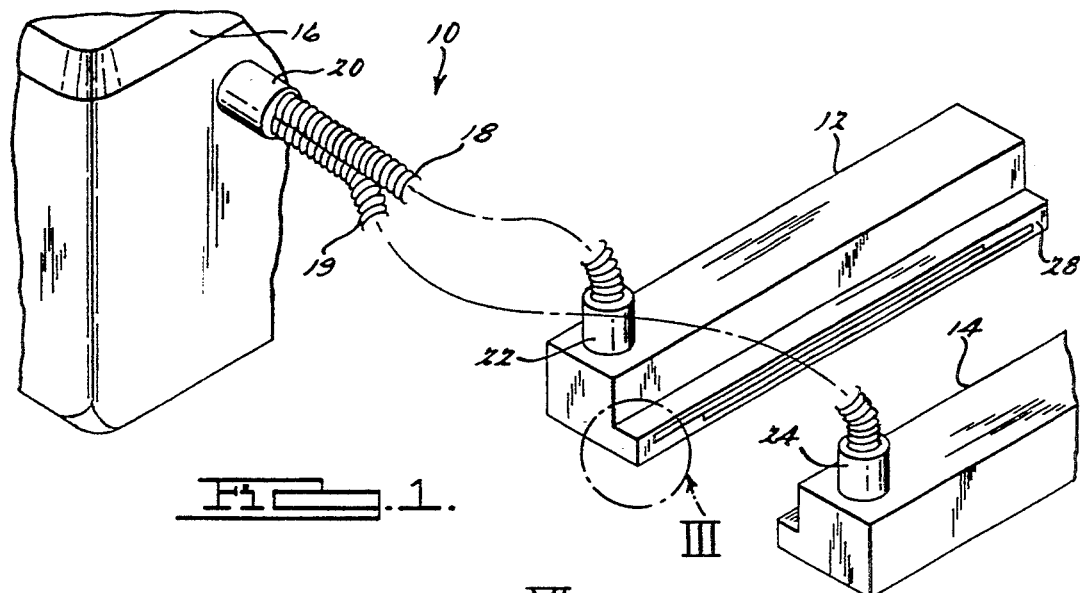
FIG. 1 is a perspective view of the distributed light delivery system of the present invention.

Referring now to the drawings wherein like components among the various views are represented by the same numeral, FIG. 1 shows the distributed light delivery system 10 of the present invention comprised of two light delivery bars 12 and 14 each connected to a light and power source 16 via flexible fiber optic bundles 18 and 19, respectively.

The preferred light and power source 16 is a MVS 2020 Machine Vision Strobe Unit purchased from EG&G Electro of Salem, Mass. and modified with three supplemental 12 uF capacitors connected in parallel (88-00-38SR) to produce more light energy. Thus modified, light and power source 16, operating on standard 110 V, 60 MHZ AC current, provides 8.64 Joules/45 Watts of energy to a 600 VDC short arc xenon flash lamp located within the housing of the light and power source 16. The optical energy emitted from the xenon lamp is concentrated through an ellipsoidal light reflector, also located within the strobe light and power source 16, for transmission through the optical fibers 27. The light reflector has a highly reflective coating to improve its optical energy coupling efficiency over that of a dull reflector thereby channeling more of the light energy from the xenon lamp into each optical fiber 27.

The preferred fiber optic bundle arrangement is a dual fiber optical bundle obtained from Fostec, Inc. of Auburn, N.Y. having a distal common input trunk 20 exiting the light and power source 16 and two proximal fiber optic legs 22 and 24 entering the light delivery bars 12 and 14, respectively. The common input trunk 20 has an active (fiber bundle) diameter of 0.68 in. providing a cross-sectional area of approximately 0.36 in$^2$. Each fiber optic leg 22 and 24 has an active diameter of approximately 0.48 in. for a cross-sectional area of 0.18 in$^2$. and is made up of optical fibers 27 which are approximately 0.002 in. in diameter.

Figure 2:
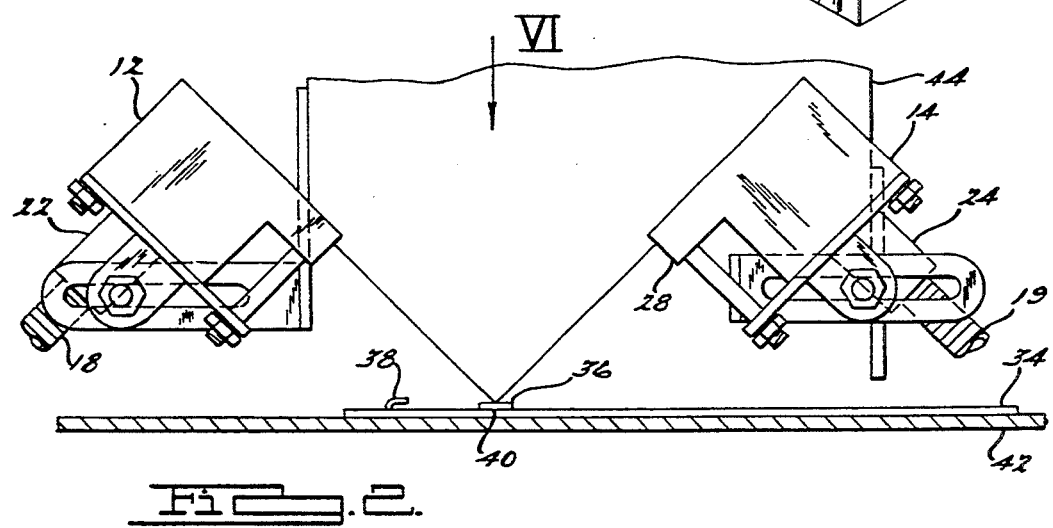
FIG. 2 is an end view of the two light delivery bars mounted in operating position on the video camera staging structure that straddles an automated conveyor transporting subject circuit boards.

Referring now to FIG. 2, a subject printed circuit board 34 is shown populated with SMD technology components 36 and discrete through-hole technology components 38 affixed to pads 40. The printed circuit board 34 is positioned on a continuous conveyor 42 that passes under a video camera staging structure 44 during a machine vision fault inspection operation.

Figure 4:
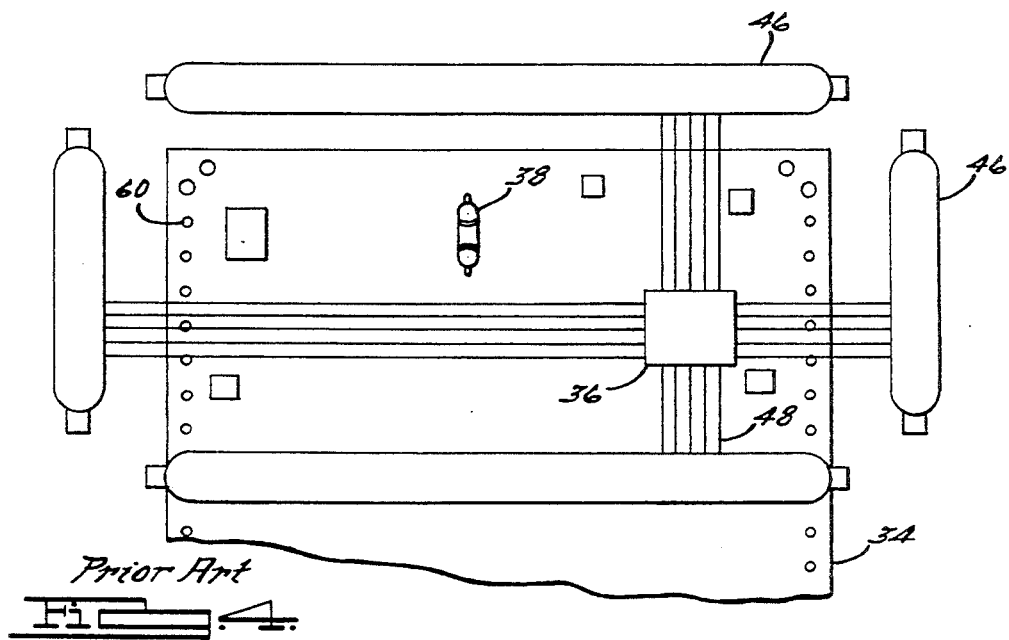
FIG. 4 is a plan view of a discrete light delivery system showing light rays incident on an individual SMD (size exaggerated) mounted on a circuit board.

As illustrated in FIG. 4, prior machine vision inspection systems used multiple discrete xenon lamps 46 that emitted light rays 48 substantially perpendicular to the faces of the SMD technology components 36 and discrete through-hole technology components 38 mounted on the subject printed circuit board 34. One xenon lamp 46 was typically arranged along each side of the printed circuit board 34 to illuminate all four sides of the three-dimensional SMD technology components 34. The use of four discrete xenon lamps in current machine vision applications proves disadvantageous due to tight space requirements. More importantly, illuminating the three-dimensional (essentially cubical) SMD components straight-on from four directions fails to provide shadow-free illumination of these objects. Shadow-free illumination is not achieved through the straight-on approach due to the fact that SMDs 36 offset from the centerline of the printed circuit board 34 are necessarily closer to one of two opposing xenon lamps 46 than to the other. Thus, the face of the SMD technology component 36 that is closer to the xenon lamp 46 is lit more intensely relative to the face on the opposite side of the SMD technology component 36 which is cast in a relative shadow as a result. To overcome this uneven light distribution problem, the discrete xenon lamp arrangement disadvantageously requires a large, high voltage power source to provide enough light to flood the board with illumination.

Figure 3:
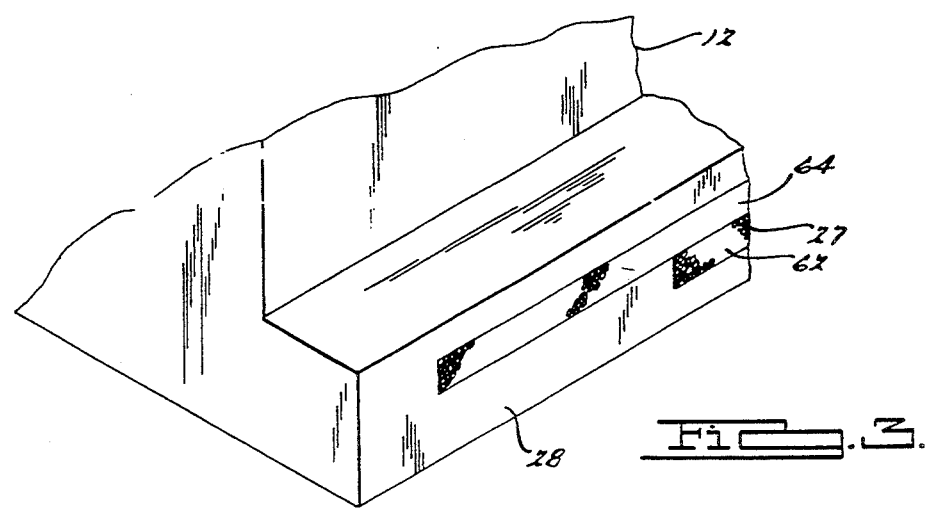
FIG. 3 is an enlarged detail of circle III in FIG. 1 showing a perspective view of the fiber optic light lines.
Figure 8:
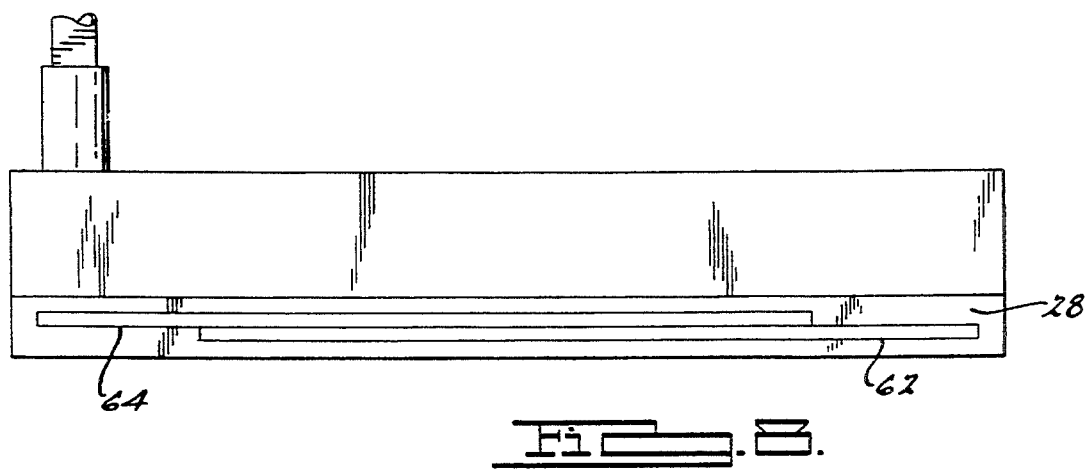
FIG. 8 is a front view of a light delivery bar showing the overlapping offset of the two fiber optic light lines.

In contrast, the light delivery bars 12 and 14 of the present invention, when properly mounted on the video camera staging structure 44, provide uniform and shadow-free illumination of the SMD technology components 36 mounted on the printed circuit board 34. Referring now to FIGS. 1, 3 and 8, each light delivery bar 12 and 14 of the preferred embodiment is approximately 11 in. long, 3 in. wide and 2 in. tall and has a front face 28 with first and second fiber optic light lines 62 and 64, respectively. Fiber optic light lines 62 and 64 emit light transmitted from the strobe light and power source 16 through each of the flexible fiber optic bundles 18 and 19, respectively. Each fiber optic light line 62 and 64 measures approximately 7.5 inches long and 0.02 inches high. Fiber optical light lines 62 and 64 are offset from opposite ends of light delivery bar 12 or 14 as shown in FIG. 8.

Figure 5:
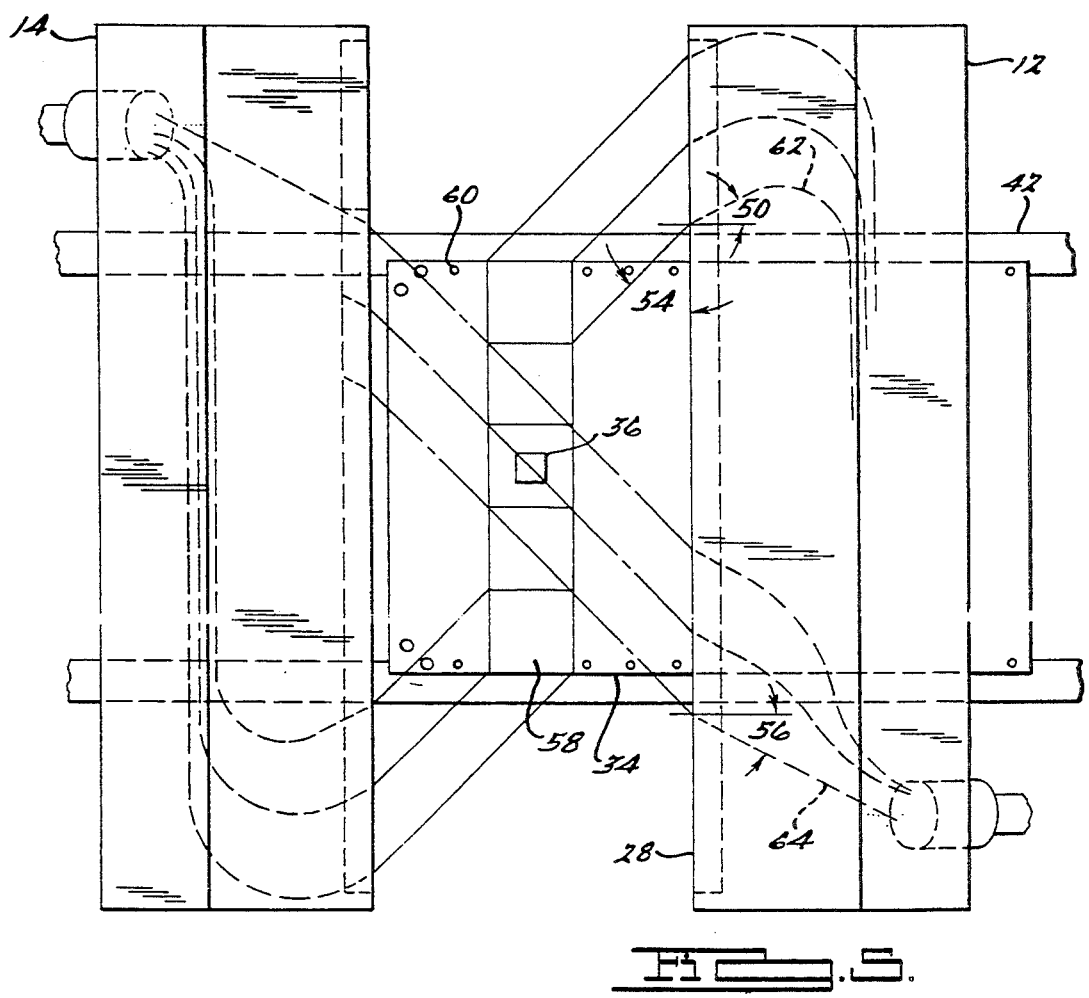
FIG. 5 is a plan view of the distributed light delivery system of the present invention showing light rays incident on an individual SMD (size exaggerated) mounted on a circuit board.
Figure 6:
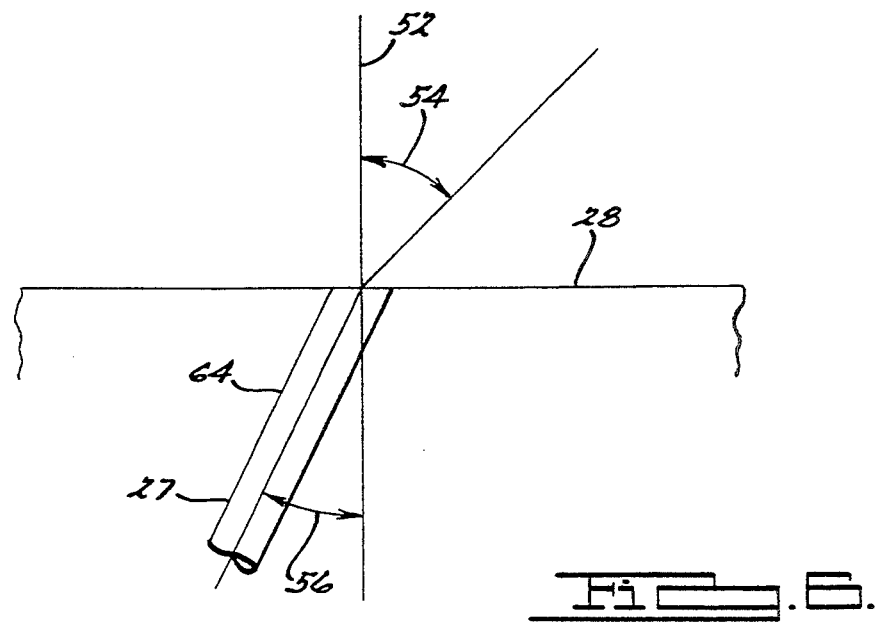
FIG. 6 is a plan view of a single optical fiber in the array of fibers within an optical light line on a light delivery bar showing the orientation of the optical fibers within the optical fiber array and the refraction of the primary light ray emitted from that optical fiber.
Figure 7:
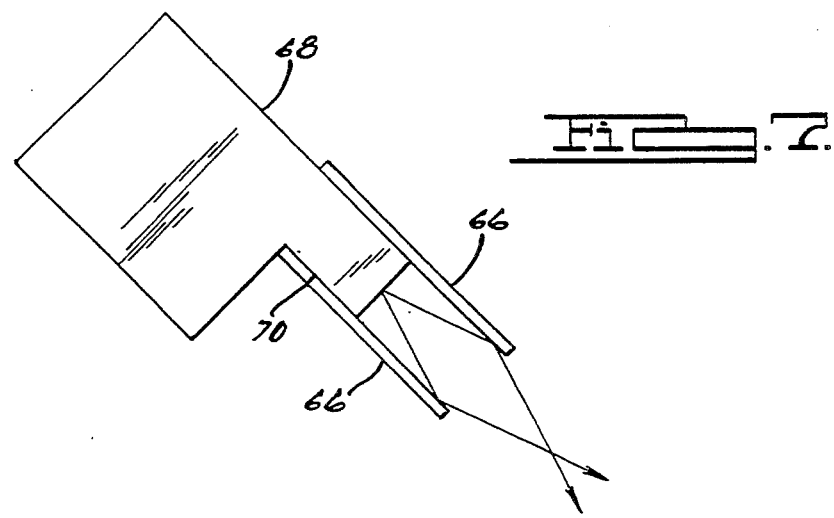
FIG. 7 is a side view of a light delivery bar showing light recovery baffles mounted thereon.

Referring now to FIGS. 3, 5, and 6, each fiber optic light line 62 and 64 is comprised of an array of individual fiber optic strands 27 embedded within the light delivery bars 12 and 14. All the individual fiber strands 27 in the first fiber optic light line 62 are embedded at the same orientation angle 50 of approximately 27 degrees relative to the normal 52 to the front face 28. The individual fiber optic strands of the second fiber optic light line 64 are all oriented in the complementary direction at an orientation angle 56 of 27 degrees measured from the opposite side of the normal 52 (i.e., 180 degrees−27 degrees=153 degrees measured from the same side of the normal 52).

As shown in FIGS. 5 and 6, the optical energy transmitted from the strobe light and power source 16 is emitted from the individual fiber optic strands 27 of the light delivery bars 12 and 14 at an exit angle 54 of approximately 45 degrees relative to the normal 50 due to the refractive index of the optical fiber glass. In the preferred embodiment, the resultant numerical aperture of the fiber optical fiber glass is 0.56.

The individual fiber optic strands 27 are continuous from the distal common input trunk 20 through the branching proximal input legs 22 and 24 terminating at the front face 28 where they are ground flush. The two proximal input legs 22 and 24 are different in length due to the asymmetrical mounting position of the power and light source 16 relative to the centerline of the video camera staging structure 44 compared to the symmetrical mounting position of the two light delivery bars 12 and 14 about this same centerline.

Referring now to FIGS. 2, 3 and 5, light delivery bars 12 and 14 are mounted on the video camera staging structure 44 in the preferred embodiment at an angle of 45 degrees for SMD component fault detection. The light delivery bars 12 and 14 are positioned slightly above and flanking the circuit board 34 to effectively illuminate both the SMDs 36 and the registration fiducials 60 along the edges of the printed circuit board 34 that are within the field of view 58 of the video cameras.

As shown in FIG. 5, light emitted from the first fiber optic light line 62 of the light delivery bar 12 is effective to illuminate two faces and the top of the three dimensional SMD technology component 36 with the same intensity. The remaining two faces and the top of the SMD technology component 36 are illuminated by the second fiber optic light line 64 on the same light delivery bar 12. The corresponding fiber optic light lines 62 and 64 on the opposite light delivery bar 14 reinforce the illumination of these surfaces. The two light delivery bars 12 and 14 thus provide shadow-free illumination of all four sides and the top of the three dimensional SMD components 36 significantly better than the use of four discrete lamps 46 emitting light straight-on to the component.

Finally, light recovery baffles 66 made of highly reflective material are attached along the top face 68 and bottom relief face 70 of each light delivery bar 12 and 14 to recover "stray" light rays that would otherwise strike the work area at points outside the field of view 58 of the video cameras. The light recovery baffles 66 are positioned along each light delivery bar 12 and 14 at an angle such that the stray light rays are reflected back toward the field of view 58 of the video camera on the printed circuit board 34 resulting in a broad beam of higher intensity light incident on the circuit board 34 within the field of view 58 of the video camera.

While the present invention has been disclosed in terms of its preferred embodiment, one skilled in the art should understand that a variation made to this disclosed embodiment may still properly fall within the scope of the present invention as defined by the claims that follow.

What is claimed is:

1. A distributed light delivery system, comprising: at least one housing bar with a front face and at least two optical light lines extending along substantially the entire length of said face, each one of said optical light lines being composed of an array of optical fibers that terminates along said front face, each one of said individual optical fibers having distal and proximal ends and a middle transmission path, said individual optical fibers of each one of said first optical light lines being oriented such that light rays are emitted at a first predetermined angle relative to the normal to said front face and said individual optical fibers of each one of said second optical light lines being oriented such that light rays are emitted at second predetermined angle relative to said normal.

2. The system of claim 1, wherein said first and second predetermined angles are substantially complementary.

3. The apparatus of claim 1, wherein said proximal ends of said optical fibers terminate flush with said front face.

4. The apparatus of claim 1, further comprising: at least one conduit collectively enclosing each one of said optical fibers along its middle transmission path.

5. The apparatus of claim 1, further comprising: a light source in optical communication with said distal ends of said optical fibers.

6. The apparatus of claim 1, further comprising: at least one light recovery baffle positioned on said housing bar at an angle such that emitted light energy diverging from said optical fibers is concentrated into an area of interest on a printed circuit board.

7. The apparatus of claim 6, wherein said light recovery baffle is made of a highly reflective material.

8. The apparatus of claim 1, further comprising a second light delivery bar with a front face and at least two optical light lines, each one of said optical light lines being composed of an array of optical fibers having distal and proximal ends and a middle transmission path, said individual optical fibers of each one of said first optical light lines being oriented such that light rays are emitted at a first predetermined angle relative to the normal to said front face and said individual optical fibers of each one of said second optical light lines being oriented such that light rays are emitted at second predetermined angle relative to said normal.

9. A method of delivering light into an area of interest on a printed circuit board having substantially rectangular components mounted thereon, comprising the steps of:
   (A) providing a bundle of optical fibers contained in a conduit, the distal ends of said optical fibers optically coupled to a power and light source, the proximal end of each one of said optical fibers extending past said conduit;
   (B) terminating said extending end of each one of said optical fibers within said light delivery housing at one of at least two predetermined angles; and
   (C) positioning said light delivery housing adjacent to said subject circuit board, to effectively illuminate all four sides and the top of said components.

* * * * *